(12) United States Patent
Mouton

(10) Patent No.: US 8,713,849 B2
(45) Date of Patent: May 6, 2014

(54) INSECT TRAP

(71) Applicant: Schalk Francois Mouton, Citrusdal (ZA)

(72) Inventor: Schalk Francois Mouton, Citrusdal (ZA)

(73) Assignee: Schalk Francois Mouton, Citrusdal (ZA)

( * ) Notice: Subject to any disclaimer, the term of this patent is extended or adjusted under 35 U.S.C. 154(b) by 0 days.

(21) Appl. No.: 13/971,033

(22) Filed: Aug. 20, 2013

(65) Prior Publication Data

US 2013/0333274 A1 Dec. 19, 2013

Related U.S. Application Data

(63) Continuation of application No. PCT/IB2012/050760, filed on Feb. 20, 2012.

(30) Foreign Application Priority Data

Feb. 21, 2011 (ZA) .................................. 2011/1357

(51) Int. Cl.
*A01M 1/18* (2006.01)
(52) U.S. Cl.
USPC ................................................... 43/108
(58) Field of Classification Search
USPC .................................................. 43/108, 107
See application file for complete search history.

(56) References Cited

U.S. PATENT DOCUMENTS

| | | | | | |
|---|---|---|---|---|---|
| 569,083 | A | * | 10/1896 | Belknap | 43/108 |
| 691,546 | A | * | 1/1902 | Hubbell | 43/108 |
| 916,106 | A | * | 3/1909 | Clark | 43/108 |
| 1,345,690 | A | * | 7/1920 | Perl | 43/108 |
| 1,863,672 | A | * | 6/1932 | Repp | 43/108 |
| 2,170,589 | A | * | 8/1939 | Erickson | 43/108 |
| 4,756,116 | A | * | 7/1988 | Cutter | 43/108 |
| 4,769,943 | A | * | 9/1988 | Simpson | 43/107 |
| 4,800,671 | A | * | 1/1989 | Olson | 43/108 |
| 5,695,807 | A | | 12/1997 | Hayes et al. | |
| 6,108,968 | A | * | 8/2000 | Peng | 47/32.5 |
| 6,223,463 | B1 | * | 5/2001 | Carlson et al. | 43/108 |

FOREIGN PATENT DOCUMENTS

AU 2005100654 A4 9/2005

OTHER PUBLICATIONS

International Application No. PCT/IB2012/050760 International Search Report and Written Opinion.

* cited by examiner

*Primary Examiner* — Christopher P Ellis
(74) *Attorney, Agent, or Firm* — Woodard, Emhardt, Moriarty, McNett & Henry LLP

(57) ABSTRACT

A method of controlling pests includes applying a trap (10) to a plant. The A trap (10) includes a tube (12) of resilient material with a longitudinal slit (16) in its outer wall (14) for at least part of the length of the tube (12) and a number of apertures (18) in the outer wall. The resilience of the outer wall (14) urges edges of the outer wall on opposing sides of the slit (16) towards each other. The trap (10) is installed by extending the tube (12) around a trunk (20) of the plant, so that its two opposing ends (22, 24) face each other, and inserting one end of the tube (22) inside the opposing end (24) by urging open the slit (16) at the outer end to enlarge the outer end and gripping the inner end by an inward resilient load from the outer wall of the outer end.

23 Claims, 1 Drawing Sheet

INSECT TRAP

CROSS-REFERENCE TO RELATED APPLICATIONS

This application is a continuation of International Patent Application No. PCT/IB2012/050760 filed Feb. 20, 2012, which claims the benefit of South Africa Patent Application No. 2011/01357 filed Feb. 21, 2011, which are hereby referenced in their entireties.

FIELD OF THE INVENTION

This invention relates to the control of insect pests and in particular, it relates to insect traps that are effective in controlling pests that crawl along plant trunks or the like, such as snout beetles (true weevils), e.g. *Eremnus setulosus* and *Phlyctinus colosus*.

BACKGROUND TO THE INVENTION

The description below refers to snout beetles as an example of pest, but many other pests show similar behavioural patterns and the present invention is applicable to a much wider variety of target pests.

Snout beetles are small insects that over-winter in the soil as pupae, which hatch in early spring and then crawl up the stems of plants such as vines or fruit trees to feed in the canopies on leafs and young fruits, causing considerable damage to crops.

Existing methods to control snout beetles and other pests with similar behaviour, include mass application of pesticides, e.g. by cover sprays of the plants (trees), which results in undesirable residue on the plants, fruits, etc. Further methods to control snout beetles include the use of barriers such as sticky materials (with insecticides) that are applied to the trunks or held in open cell absorbent bands, in which the snout beetles become trapped as they crawl along the trunks. However, sticky materials are cumbersome to apply and lose their effectiveness when exposed to the elements and need to be touched up regularly. Likewise, the absorbent bands do not retain the sticky materials and insecticides when they are exposed to the elements—especially near their surfaces, where the snout beetles crawl.

The present invention seeks to provide effective, long lasting, cost effective and convenient control of snout beetles and similarly behaving pests.

SUMMARY OF THE INVENTION

According to one aspect of the present invention there is provided a trap comprising a tube of resiliently deformable material, said tube including an outer wall extending around an inner cavity and said tube defining a longitudinal slit in the outer wall, extending between the inner cavity and an outside of the tube for at least part of the length of the tube, the resilience of the outer wall urging edges of the outer wall on opposing sides of the slit towards each other, said outer wall defining a plurality of apertures, each extending between the inner cavity and the outside of the tube.

The cross-sectional profile of the tube may be round, or it may have any other shape.

A pest control substance, such as a pesticide and/or attractant may be provided inside the inner cavity of the trap, e.g. a pesticide and attractant may be embedded in a carrier substance such as petroleum gel inside the inner cavity.

The pest control substance may include an odorant substance for use in as an attractant for snout beetles, and the odorant substance may include at least one of the following compounds:
Cyclopropane carboxylic acid;
5-Methyl-2-hexanone;
2,5-Dimethyl-4-methoxy-3(2H)-furanone;
Anisole; and
3-Methoxy acetophenone.

The odorant substance may includes each of the compounds: Cyclopropane carboxylic acid, 5-Methyl-2-hexanone, 2,5-Dimethyl-4-methoxy-3(2H)-furanone, and Anisole and these compounds may be included in the odorant substance in generally equal parts, by volume and may be contained in a capsule with a polymeric wall through which the compounds can pass by diffusion.

Instead, or in addition, the odorant substance may include 20% 3-Methoxy acetophenone, diluted in water, by volume.

The odorant substance may include each of the compounds: Cyclopropane carboxylic acid, 5-Methyl-2-hexanone, 2,5-Dimethyl-4-methoxy-3(2H)-furanone, Anisole, and 3-Methoxy acetophenone.

The outer wall may include circumferential ribs and/or grooves.

According to another aspect of the present invention there is provided a method of controlling pests by applying a trap as described hereinabove to a plant, by:
extending the tube around a trunk of the plant, so that it has two opposing ends that face each other, the length of the tube being longer than the circumference of the trunk; and
inserting one end of the tube inside the inner cavity of the opposing end of the tube so that the ends of the tube form an inner end and an outer end, by urging open the slit at the outer end to enlarge the outer end and gripping the inner end by an inward resilient load from the outer wall of the outer end.

The word "trunk" refers in this context to a tree trunk or any other branch or stem of a plant, along which the target pests may crawl.

The method may include the step of cutting the tube to a suitable length.

The method may include placing a capsule containing at least one of Cyclopropane carboxylic acid, 5-Methyl-2-hexanone, 2,5-Dimethyl-4-methoxy-3(2H)-furanone, and Anisole inside the inner cavity of the trap, and the capsule may have a polymeric wall through which these compounds can pass by diffusion. The capsule may contain each of the Cyclopropane carboxylic acid, 5-Methyl-2-hexanone, 2,5-Dimethyl-4-methoxy-3(2H)-furanone, and Anisole in generally equal parts, by volume.

The method may include applying a 20% dilution of said 3-Methoxy acetophenone in water, by volume, to an inner surface of the wall of the trap.

A method may include combining the odorant substance with an insecticide.

The pest for which the trap is used may be snout beetle, e.g. *Eremnus setulosus* and/or *Phlyctinus calosus*.

BRIEF DESCRIPTION OF THE DRAWINGS

For a better understanding of the present invention, and to show how the same may be carried into effect, the invention will now be described by way of non-limiting example, with reference to the accompanying drawings in which.

DETAILED DESCRIPTION OF THE DRAWINGS

Figure 2:
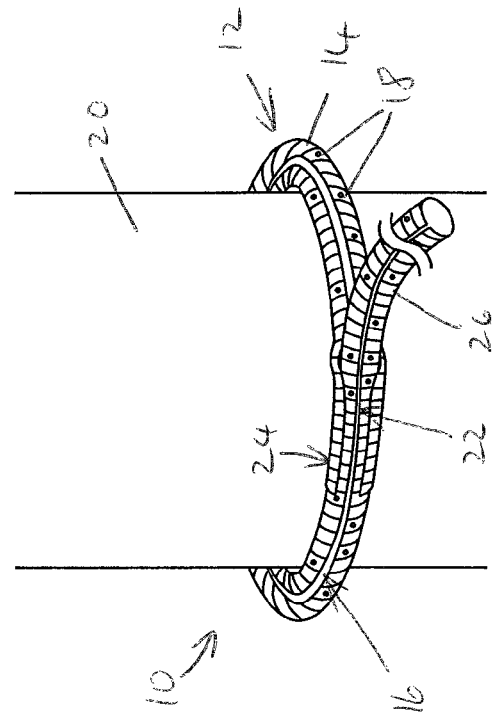
FIG. 2 shows the trap of FIG. 1, with indeterminate length, partly applied around the trunk.
Figure 1:
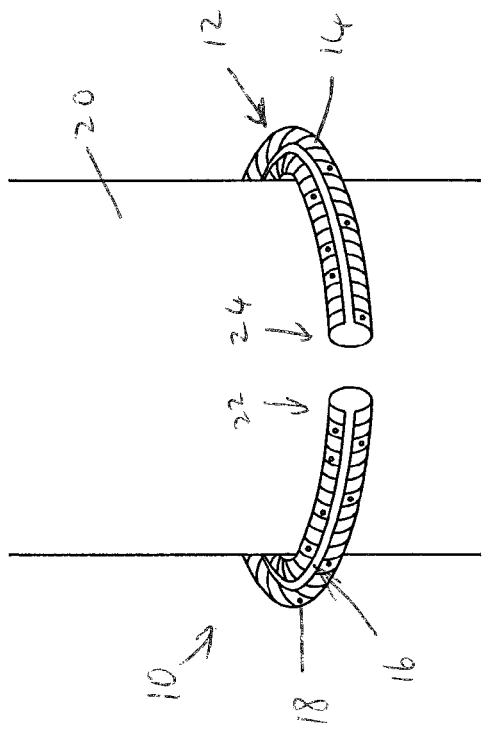
FIG. 1 shows a trap in accordance with the present invention, extending partly around a trunk.

Referring to the drawings, a trap in accordance with the present invention is generally indicated by reference numeral 10.

The trap 10 includes a hollow tube 12, with a generally cylindrical outer wall or side wall 14 and a hollow internal cavity. The tube need not be cylindrical, but in a preferred embodiment, it is a ribbed tube of resilient plastic material with a nominal diameter of about 14 mm—of a type commonly used as conduits for housing electrical conductors.

A longitudinal slit 16 is defined in the wall 14 of the tube 12, which extends the entire length of the tube, although the slit need not extend the entire length of the tube in some embodiments (see below).

The wall 14 is perforated with a plurality of apertures 18 that extend between the inner cavity and the outside of the tube 12 and inside the internal cavity, a pest control composition is provided, typically in the form of a carrier substance such as petroleum gel in which an odorant attractant and a pesticide are embedded. (See example of pest attractant below.) The diameters of the apertures 18 are selected to suit the target pests, e.g. for small insects such as snout beetles such as: *Eremnus setulosus* or *Phlyctinus calosus*, the diameters could be about 2 mm.

The trap 10 is applied to a plant by cutting the tube 12 to a suitable length, so that it can extend around the plant's trunk 20, with some overlap—i.e. the length of the tube must be more than the circumference of the trunk. The tube 12 is positioned so that it extends around the trunk 20 so that its two opposing ends face each other and form an inner end 22 and an outer end 24. The inner end 22 is inserted inside the cavity of the outer end 24 by urging the slit 16 open at the outer end and the resilience of the tube 12 urges the slit to close again, so that the wall at the outer end 24 applies an inward load on the inner end 22, which grips it and holds the ends 22, 24 together.

In the illustrated embodiment, where the tube 12 is ribbed, the consecutive ribs and grooves on the inside of the wall at the outer end 24, engage the ribs and grooves on the outside of the inner end 22—thus enhancing the grip between the ends 22, 24.

As shown in FIG. 2, instead of cutting the tube 12 to a desired length before installing it, a tube of indeterminate length can be used and the inner end 22 inserted inside the outer end with a desirable length of tube extending around the trunk 20, before cutting the tube. In the illustrated example, an excess length 26 of the tube 12 needs to be cut from the inner end 22.

The slit 16 need not extend the entire length of the tube 12, but is only needed at the outer end 24, to allow it to open up and receive the inner end 22. However, if the slit 16 extends the entire length of the tube 12, it means that the tube can be provided in a very long length, from which shorter tubes can be cut at any point, to form shorter tubes of suitable lengths to extend around trunks 20, thus avoiding the wastage that would result if excess material 26 has to be removed from each individual tube.

Once the trap 10 has been installed around the trunk 20 (preferably tightly against the trunk), insects such as snout beetles crawling along the trunk need to cross the tube 12 to reach the plant's canopy, from the ground. The insects enter the inner cavity of the trap 10 via the apertures 18, either through random exploration while searching for food, or under attraction from the odorant attractant inside the cavity. Once inside the cavity, the insects are exposed to the insecticides and die.

The attractants used inside the inner cavity of the trap 10 may be attractants as described in International Patent Application No. PCT/IB2012/050610—the contents of which is included herein in its entirely, by reference.

In a preferred embodiment of the present invention, in which the trap 10 is intended to control pests in the form of snout beetles such *Eremnus setulosus* or *Phlyctinus calosus*, the attractants could be prepared by:

Combining equal parts of the compounds Cyclopropane carboxylic acid, 5-Methyl-2-hexanone, 2,5-Dimethyl-4-methoxy-3(2H)-furanone, and Anisole, by volume and using the combination to fill capsules with polymeric walls that are sufficiently pervious to serve as reticular diffusion membranes, through which the compounds can escape very slowly by diffusion, over extended periods; and/or Diluting 3-Methoxy acetophenone in a 20% solution in water.

The 3-Methoxy acetophenone solution can be applied to the inner surfaces of the wall 14, facing the inner cavity, and the filled capsules can be placed inside the inner cavity. The applicant believes that each of the active ingredients of these attractants, Cyclopropane carboxylic acid, 5-Methyl-2-hexanone, 2,5-Dimethyl-4-methoxy-3(2H)-furanone, Anisole, and 3-Methoxy acetophenone can serve as an attractant for snout beetles on its own, but that these attractants act synergistically when used in combination, to attract even greater numbers of snout beetles.

The invention holds the advantages of low cost of the trap 10 and convenient installation around a variety of shapes and sizes of trunks 20. Further, the protection of the pest control composition inside the cavity prevents it from being washed away, dried or otherwise rendered ineffective by the elements and thus provides long lasting pest control.

The invention claimed is:

1. A trap (10) comprising a tube (12) of resiliently deformable material, said tube including an outer wall (14) extending around an inner cavity and said tube defining a longitudinal slit (16) in the outer wall, extending between the inner cavity and an outside of the tube for at least part of the length of the tube, the resilience of the outer wall urging edges of the outer wall on opposing sides of the slit towards each other, said outer wall defining a plurality of apertures (18), each extending between the inner cavity and the outside of the tube.

2. A trap as claimed in claim 1, characterised in that the cross-sectional profile of the tube (12) is round.

3. A trap as claimed in claim 1, characterised in that a pest control substance is provided inside the inner cavity.

4. A trap as claimed in claim 3, characterised in that said pest control substance includes a pesticide.

5. A trap as claimed in claim 3, characterised in that said pest control substance includes an attractant.

6. A trap as claimed in claim 3, characterised in that said pest control substance is embedded in a carrier substance inside the inner cavity.

7. A trap as claimed in claim 5, characterised in that said pest control substance includes an odorant substance for use in as an attractant for snout beetles, said odorant substance including at least one of the following compounds:

Cyclopropane carboxylic acid;
    5-Methyl-2-hexanone;
    2,5-Dimethyl-4-methoxy-3(2H)-furanone;
    Anisole; and
    3-Methoxy acetophenone.

8. A trap as claimed in claim 7, characterised in that said odorant substance includes each of the compounds: Cyclopropane carboxylic acid, 5-Methyl-2-hexanone, 2,5-Dimethyl-4-methoxy-3(2H)-furanone, and Anisole.

9. A trap as claimed in claim 8, characterised in that said compounds are included in said odorant substance in generally equal parts, by volume.

10. A trap as claimed in claim 8, characterised in that said odorant substance is contained in a capsule with a polymeric wall through which said compounds can pass by diffusion.

11. A trap as claimed in claim 7, characterised in that said odorant substance includes 20% 3-Methoxy acetophenone, diluted in water, by volume.

12. A trap as claimed in claim 7, characterised in that said substance includes each of the compounds: Cyclopropane carboxylic acid, 5-Methyl-2-hexanone, 2,5-Dimethyl-4-methoxy-3(2H)-furanone, Anisole, and 3-Methoxy acetophenone.

13. A trap as claimed in claim 1, which includes circumferential ribs.

14. A trap as claimed in claim 1, which includes circumferential grooves.

15. A method of controlling pests by applying a trap (10) as claimed in claim 1 to a plant, said method comprising the steps of:
    extending the tube (12) around a trunk (20) of the plant, so that it has two opposing ends (22,24) that face each other, the length of the tube being longer than the circumference of the trunk; and
    inserting one end of the tube (22) inside the inner cavity of the opposing end (24) of the tube so that the ends of the tube form an inner end (22) and an outer end (24), by urging open the slit (16) at the outer end to enlarge the outer end and gripping the inner end by an inward resilient load from the outer wall of the outer end.

16. A method as claimed in claim 15, characterised by the step of cutting the tube (12) to a suitable length.

17. A method as claimed in claim 15, characterised by placing an odorant substance comprising a capsule containing at least one of Cyclopropane carboxylic acid, 5-Methyl-2-hexanone, 2,5-Dimethyl-4-methoxy3(2H)-furanone, and Anisole inside the inner cavity of said trap, said capsule having a polymeric wall through which said compounds can pass by diffusion.

18. A method as claimed in claim 17, characterised in that each of said Cyclopropane carboxylic acid, 5-Methyl-2-hexanone, 2,5-Dimethyl-4-methoxy3(2H)-furanone, and Anisole is contained in said capsule, in generally equal parts, by volume.

19. A method as claimed in claim 15, characterised by applying an odorant substance comprising a 20% dilution of 3-Methoxy acetophenone in water, by volume, to an inner surface of the wall (14) of said trap (10).

20. A method as claimed in claim 17, characterised by combining said odorant substance with an insecticide.

21. A method as claimed in claim 15, characterised in that the pest is snout beetle.

22. A method as claimed in claim 21, characterized in that the snout beetle is *Eremnus setulosus*.

23. A method as claimed in claim 21, characterized in that the snout beetle is *Phlyctinus calosus*.

* * * * *